(12) United States Patent
Giuliani et al.

(10) Patent No.: US 9,192,595 B2
(45) Date of Patent: *Nov. 24, 2015

(54) COMPOUNDS WITH A SKIN PIGMENTING ACTIVITY AND PHARMACEUTICAL OR COSMETIC COMPOSITIONS CONTAINING THEM

(75) Inventors: Giammaria Giuliani, Milan (IT); Ralf Paus, Hamburg (DE); Yuval Ramot, Mevasseret-zion (IL); Astrid Becker, Luebeck (DE); Sergio Baroni, Villa D'adda (IT)

(73) Assignee: GIULIANI S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/807,970

(22) PCT Filed: Jul. 15, 2011

(86) PCT No.: PCT/EP2011/062129
§ 371 (c)(1),
(2), (4) Date: Jan. 2, 2013

(87) PCT Pub. No.: WO2012/007572
PCT Pub. Date: Jan. 19, 2012

(65) Prior Publication Data
US 2013/0108564 A1    May 2, 2013

(30) Foreign Application Priority Data

Jul. 16, 2010 (EP) .................... 10425243

(51) Int. Cl.

| A61K 31/232 | (2006.01) |
| A61K 8/36 | (2006.01) |
| A61K 8/37 | (2006.01) |
| A61K 31/202 | (2006.01) |
| A61Q 17/04 | (2006.01) |
| A61Q 19/04 | (2006.01) |
| A61K 31/192 | (2006.01) |

(52) U.S. Cl.
CPC ............. *A61K 31/232* (2013.01); *A61K 8/361* (2013.01); *A61K 8/37* (2013.01); *A61K 31/192* (2013.01); *A61K 31/202* (2013.01); *A61Q 17/04* (2013.01); *A61Q 19/04* (2013.01)

(58) Field of Classification Search
CPC ....... A61K 8/361; A61K 8/37; A61K 31/202; A61K 31/192
USPC ................ 424/59; 514/544, 549, 552, 56
See application file for complete search history.

(56) References Cited

U.S. PATENT DOCUMENTS

2005/0175555 A1* 8/2005 Stradi et al. .............. 424/59

FOREIGN PATENT DOCUMENTS

| WO | 03/095403 | 11/2003 |
| WO | 2010/052328 | 5/2010 |
| WO | 2010/052329 | 5/2010 |

OTHER PUBLICATIONS

Bissett, D.L., et al., "Protective effect of topically applied conjugated hexadienes against ultraviolet radiation-induced chronic skin damage in the hairless mouse", Protcor & Gamble Company, Miami Valley Laboratories, Dermatology Department, College of Medicine, University of Cincinnati, Cincinnati, OH, USA, pp. 63-67, vol. 7, 1990. Jun. 12, 2014.

Enrica, F. et al., "2, 4, 6-octatrienoic acid promotes melanogenesis in normal human melanocytes", Journal of Investigative Dermatology; 40th Annual Meeting of the European Society for Dermatological Research, Helsinki, Finland, Sep. 8-11, 2010, Nature Publishing Group, GB, vol. 130, No. 2, p. S98.

Giuliani, G. et al., "Treatment of the severe photodamage", Journal of Investigative Dermatology; Annual Meeting of the Society for Investigative Dermatology, Atlanta, GA, May 5-8, 2010, Nature Publishing Group, GB, vol. 130, No. 2, p. S40.

Kollias, N. et al., "New Trends in Photobiology", Journal of Photochemical Photobiology B: Biology, vol. 9, pp. 135-160, 1991.

Pini, E. et al., "Biological Activity of Parrodienes, a New Class of Polyunsaturated Linear Aldehydes Similar to Carotenoids", Drugs Under Experimental and Clinical Research, vol. XXX, pp. 203-206, 2004.

* cited by examiner

*Primary Examiner* — Johann R Richter
*Assistant Examiner* — Yanzhi Zhang
(74) *Attorney, Agent, or Firm* — Fish & Tsang, LLP (57) ABSTRACT

The present invention relates to compounds having general formula (I):

$$CH_3-(CH=CH)_n-R \qquad (I)$$

where: n=3, 5, 7; R is chosen from $-CH_2-O-CO-R'$, $-CO-OR'$ or $-CO-O^{(-)}$,

R' is chosen from H, $C_1$-$C_{22}$ alkyl or alkenyl, aryl or aralkyl, or sugars; and their pharmaceutically acceptable salts, such as sodium, potassium and lysine salts, for use as the active ingredient in pharmaceutical or cosmetic compositions for improving the pigmentation of the human skin, treating pigmentation disorders and/or improve both the photoprotective capacity of the skin and the intensity of its suntan.

10 Claims, 5 Drawing Sheets

COMPOUNDS WITH A SKIN PIGMENTING ACTIVITY AND PHARMACEUTICAL OR COSMETIC COMPOSITIONS CONTAINING THEM

This application is a National Phase filing of PCT Application No. PCT/EP11/62129 filed on Jul. 15, 2011, which claims priority to European Application No. 10425243.2, filed on Jul. 16, 2010, which are both incorporated herein by reference in their entirety.

FIELD OF THE INVENTION

This invention relates to compounds with a skin pigmenting activity, which are useful as active ingredients in the preparation of pharmaceutical or cosmetic compositions for the treatment of pigmentation disorders, or with photoprotective properties.

STATE OF THE ART

Skin pigmentation and its photoprotective capacity depend not only on the type and quantity of melanin synthesised by the melanocytes, but also on differences in the size, number and distribution pattern of the melanosomes in the surrounding keratin cells. Melanin synthesis, or melanogenesis, is an enzymatic process that is catalysed by the tyrosinases TRP1 (tyrosinase-related protein 1) and TRP2 (tyrosinase-related protein 2), which convert thyroxin into melanic pigment in melanosomes. The induction of these enzymes potentiates the biosynthesis of melanin, and of eumelanin in particular, which is the pigment with photoprotective properties against the harmful effects of ultraviolet radiation (UV) Skin cancer is known to be one of the most common tumours, but it is also one of the easiest to prevent. Although protection against ultraviolet radiation can considerably reduce this risk, the rate of exposure to sunlight without protection still remains high.

Since the desire for a suntan often overrides any health concerns in those who enjoy sunbathing, very few measures have succeeded so far in changing this type of behaviour. Sunless tanning with self-tanners and spray-on tans are methods for achieving a suntanned appearance without exposure to UV radiation and might represent an effective addition to measures for the prevention of melanoma.

As reported by Fu, Dusza and Halpern, J. Am. Acad. Dermatol., volume 50, issue No. 5, enhanced awareness of the negative effects of UV radiation is promoting the rapid growth of a sunless tanning industry. A novel technology recently introduced by this industry, for instance, is the sunless tanning booth, in which a fine sprayer devices enable an even coating of sunless tanning solution to be applied to the skin.

Another valid approach to preventing the damage caused by exposure to the sun is to increase the production of melanin, thereby obtaining a natural photoprotective action.

A reference on photoprotective melanin and epidermal melanin pigmentation (EMP) can be found in the Journal of Photochemistry and Photobiology B: Biology, volume 9, issue No. 2, May 1991, Pages 135-160, *New trends in photobiology: Photoprotection by melanin*, Nikiforos Kollias, Robert M. Sayre, Lisa Zeise & Miles R. Chedekel.

Among the other diseases commonly involving the skin, there are pigmentation disorders involving certain areas of the skin, pigmentation changes or lesions that change colour, only occasionally associated with a systemic disease, although pigmentation can sometimes be indicative of severe disease. Although pigmentation changes may only be considered merely as a cosmetic issue, it is important to remember that they can also be a source of embarrassment and great emotional stress to patients.

One of the most frequently reported pigmentation disorders is vitiligo, in which distinct areas of the skin and mucous membranes lack pigmentation. This loss of pigmentation may be local or general; the disease tends to be progressive and can be emotionally disabling to patients.

Pityriasis alba is a skin condition common in children that usually becomes apparent before puberty. Typical lesions of pityriasis alba are hypopigmented patches or macules with a slight tendency to flakiness, primarily on the face and, less frequently, on the neck, trunk, and extremities.

Idiopathic guttate hypomelanosis involves the appearance of depigmented macules, particularly on the arms and legs. These irregularly-shaped macules are basically common in light-skinned individuals who have been intensively exposed to sunlight, with a prevalence in women.

Post-inflammatory hypopigmentation originates from inflammatory conditions that alter melanocyte function, thus leading to patchy changes in pigmentation, which may be hyper- or hypo-pigmented.

Bourneville's syndrome (tuberous sclerosis) is a congenital disease characterised by seizures, mental retardation and adenoma sebaceum. Patients often have hypopigmented macules, usually located on the arms, legs and trunk. These lesions are a key finding in Bourneville's syndrome and may be the first clinical signs of the disease.

Tinea versicolor is a ubiquitous skin disease. Patients often notice pigment changes during the summer months and may refer to these areas of decreased pigmentation as sun spots. This disorder presents as macules and patches of decreased pigmentation associated with a fine flakiness. The lesions tend to be round or scalloped in shape. The areas affected are usually asymptomatic, but patients may sometimes complain of pruritus.

SUMMARY OF THE INVENTION

According to the present invention, it has been unexpectedly found that compounds having the following general formula (I) possess a skin pigmenting activity useful in the treatment of disorders of the above-mentioned type, or for use as photoprotective agents against UV radiation:

$$CH_3-(CH=CH)_n-R \quad (I)$$

where: n=3, 5, 7; R is chosen from $-CH_2-O-CO-R'$, $-CO-OR'$ or $-CO-O^{(-)}$, R' being chosen from H, $C_1$-$C_{22}$ alkyl or alkenyl, aryl or aralkyl, or sugars; and their pharmaceutically acceptable salts, such as sodium, potassium and lysine salts.

DETAILED DESCRIPTION OF THE INVENTION

An experimental study reported below surprisingly shows that the compounds of the invention can significantly induce an epidermal melanogenesis activity via a non-receptor pathway.

The invention also relates to pharmaceutical and cosmetic compositions thereof, each compound having general formula (I) being used as such, or mixed with the others.

The invention thus refers to the use of compounds with the formula (I) as active ingredients for all therapeutic or cosmetic applications in which a melanogenic activity produces a beneficial effect, with special reference to uses for the treatment of the above-mentioned epidermal pigmentation disorders, and particularly vitiligo, pityriasis alba, idiopathic guttate hypomelanosis, post-inflammatory hypopigmentation, Bourneville's syndrome (tuberous sclerosis) and tinea versicolor.

In a different cosmetic use according to the present invention, said melanogenic activity is useful for producing a sunless tanning effect in lieu of a suntan.

Moreover, the invention envisages the use of compounds with the general formula (I) as photoprotective agents against the harmful effect of ultraviolet (UV) radiation on the skin.

One composition of the invention, which is preferably formulated for topical administration on the skin, includes said active ingredient in quantities in the range of 0.01-2% by weight of the composition.

The characterisation data and formulas for some of the preferred compounds with the general formula (I) are given below as a non-limiting description of the invention.

The following are non-limiting examples of compositions particularly suitable for the above uses.

The quantities of the ingredients, which are identified according to the INCI nomenclature, are expressed as weight percentages, which may vary within the stated ranges.

Example 1

Gel for Topical Application

| Component (INCI name) | % w/w |
|---|---|
| C10-30 Alkyl acrylate crosspolymer | 0.05-0.30 |
| Denatured alcohol | 0.50-5.00 |
| Phospholipids. | 0.50-2.50 |
| Octatrienoic acid | 0.05-0.30 |
| PEG-8 caprylic/capric glycerides | 0.10-0.30 |
| Sodium hydroxymethylglycinate | 0.40-0.50 |
| Aqua | q.s.100 |

The pH of the formula is adjusted to pH = 6 with lactic acid (if necessary).

Example 2

Hydro-Alcoholic Gel

| Component (INCI name) | % w/w |
| --- | --- |
| Carbomer | 0.10-1.50 |
| Disodium EDTA | 0.02-0.05 |
| Denatured alcohol | 5.00-20.00 |
| Octatrienoic acid, potassium salt | 0.05-0.30 |
| Triethanolamine | 0.15-2.25 |
| Aqua | q.s. 100 |

The pH of the formula is adjusted to pH = 5.5 with triethanolamine (if necessary).

Example 3

Cosmetic Emulsion

| Component (INCI name) | % w/w |
| --- | --- |
| Disodium EDTA | 0.05-0.10 |
| Carbomer | 0.10-0.40 |
| Octatrienoic acid L-lysine salt | 0.05-0.30 |
| PEG-8 beeswax | 5.00-14.00 |
| Isostearyl isostearate | 5.00-10.00 |
| Caprylic/capric triglyceride | 5.00-10.00 |
| Phenoxyethanol | 0.30-0.90 |
| Lactic acid | 0.10-0.50 |
| Sodium hydroxymethylglycinate | 0.20-0.45 |
| Ascorbyl palmitate | 0.001-0.005 |
| Parfum | 0.20-0.50 |
| Lactic acid | 0.30-0.90 |
| Aqua | q.s. 100 |

The pH of the formula is adjusted to pH = 5.5 with sodium hydroxide solution or lactic acid (if necessary).

Example 4

Body Lotion

| Component (INCI name) | % w/w |
| --- | --- |
| Steareth-2 | 1.00-4.00 |
| Steareth-21 | 1.00-4.00 |
| Glycerin | 1.00-5.00 |
| Hydroxypropyl guar | 0.05-0.30 |
| Dicapryl carbonate | 0.50-2.00 |
| Hydrogenated lecithin | 0.05-0.80 |
| Phenoxyethanol | 0.10-0.50 |
| Caprylyl glycol | 0.10-0.70 |
| Sodium hydroxymethylglycinate | 0.10-0.50 |
| Caprylic/capric triglycerides | 1.00-5.00 |
| Isostearyl isostearate | 1.00-5.00 |
| Denatured alcohol | 0.10-4.00 |
| Disodium EDTA | 0.05-0.10 |
| Octatrienoic acid | 0.01-0.05 |
| Dimethicone | 0.50-2.00 |
| Aqua | q.s. 100 |

The pH of the formula is adjusted to pH 6 with sodium hydroxide or lactic acid (if necessary).

Example 5

Moisturising Cream

| Component (INCI name) | % w/w |
| --- | --- |
| Glycerin | 2.00-5.00 |
| Diglycerin | 1.00-3.00 |
| Cetearyl alcohol | 0.50-2.00 |
| Cetearyl glucoside | 1.00-5.00 |
| PEG-100 stearate | 1.00-5.00 |
| Tetrasodium glutamate diacetate | 0.10-0.50 |
| Octatrienoic acid | 0.05-0.50 |
| Hydrogenated Evening Primrose Oil | 0.50-3.00 |
| Octyldodecanol | 0.50-3.00 |
| Isostearyl isostearate | 1.00-4.00 |
| Caprylic/capric triglycerides | 1.00-4.00 |
| Acrylates/C10-30 alkyl acrylate crosspolymer | 0.10-0.50 |
| Sodium hydroxyde | 0.04-0.20 |
| Butyrospermum parkii | 1.00-5.00 |
| Delta tocopherol | 0.05-0.20 |
| Dimethicone | 0.50-1.50 |
| Ethylhexylglycerin | 0.25-0.50 |
| Phenoxyethanol | 0.50-0.99 |
| Parfum | q.s. |
| Aqua | q.s. 100 |

The pH of the formula is adjusted to pH 6 with sodium hydroxide acid (if necessary).

Example 6

Body Emulsion

| Component (INCI name) | % w/w |
| --- | --- |
| Glycerin | 1.00-6.00 |
| Propylene glycol | 1.00-6.00 |
| Cetyl hydroxyethylcellulose | 0.10-0.40 |
| Xanthan gum | 0.10-0.40 |
| Tapioca starch | 1.00-2.00 |
| Disodium EDTA | 0.025-0.20 |
| Sorbitan stearate | 2.00-5.00 |
| Sucrose cocoate | 0.10-1.00 |
| Ethylexyl palmitate | 1.00-5.00 |
| Hydrogenated polydecene | 1.00-5.00 |
| Caprylic/capric triglycerides | 1.00-5.00 |
| Butyrospermum parkii | 1.00-5.00 |
| Isostearyl isostearate | 1.00-5.00 |
| Dimethicone | 1.00-3.00 |
| Sodium hydroxymethylglycinate | 0.10-0.20 |
| Phenoxyethanol | 0.70-0.90 |
| Parfum | 0.30 |
| Delta tocopherol | 0.02-0.25 |
| Sorbityl furfural | 0.10-0.90 |
| Aqua | q.s. 100 |

The pH of the formula is adjusted to pH = 6.0 with lactic acid.

Example 7

Pharmaceutical Ointment

| Component (INCI name) | % w/w |
| --- | --- |
| Paraffinum liquidum | 1.00-5.00 |
| Petrolatum | 1.00-5.00 |
| PEG-8 | 5.00-75.00 |
| PEG-40 | 2.00-30.00 |
| PEG-75 | 1.00-10.00 |
| 2,4,6-Octatrien-1-ol, palmitate (octatrienyl palmitate) | 0.05-0.50 |

Example 8

Pharmaceutical Emulsion

| Component (INCI name) | % w/w |
| --- | --- |
| Phenoxyethanol | 0.70-0.99 |
| Paraffinum liquidum | 1.00-5.00 |
| Glycerin | 3.00-5.00 |
| Cetearyl alcohol | 1.00-5.00 |
| PEG-8 | 5.00-30.00 |
| PEG-40 | 5.00-30.00 |
| PEG-75 | 5.00-45.00 |
| 2,4,6-Octatrien-1-ol, acetate (octatrienyl acetate) | 0.05-0.50 |
| Aqua | q.s. 100.00 |

Example 9

Self-Tanner

| Component (INCI name) | % w/w |
| --- | --- |
| Glycerin | 2.00-5.00 |
| Dihydroxyacetone | 3.50 |
| Caprylic/capric triglycerides | 5.0-12.00 |
| Steareth-20 | 0.20-3.00 |
| Octatrienoic acid | 0.05-0.50 |
| Glyceryl monostearate | 0.50-5.00 |
| Diethylamino hydroxybenzoyl hexyl benzoate | 1.00-5.00 |
| C12-15 alkyl benzoate | 5.00-15.00 |
| Cetyl alcohol | 0.50-3.00 |
| Methylparaben | 0.01-0.15 |
| Propylparaben | 0.01-0.05 |
| Sodium hydroxide | q.s. |
| Parfum | 0.20 |
| Methylpropanediol | 1.00-6.00 |
| Aqua | q.s. 100 |

Example 10

High-Grade Sunscreen

| Component (INCI name) | % w/w |
| --- | --- |
| PEG-30 dipolyhydroxystearate | 1.00-5.00 |
| Polyglyceryl-4 diisostearate polyhydroxystearate sebacate | 2.00-5.00 |
| Ethylhexyl salicylate | 2.00-5.00 |
| Ethylhexyl methoxycinnamate | 6.00-10.00 |
| Caprylic/capric triglyceride | 3.00-10.00 |
| Butylene glycol dicaprylate/dicaprate | 3.00-6.00 |
| Diisopropyl sebacate glyceryl behenate/eicosadioate | 2.00-6.00 |
| Pentaerythrityl tetra-di-T-butyl hydroxyhydrocinnamate | 0.02-0.06 |
| Butyl methoxydibenzoylmethane | 1.00-5.00 |
| Diethylamino hydroxybenzoyl hexyl benzoate | 5.00-9.00 |
| Ethylhexyl triazone | 1.00-5.00 |
| Octocrylene | 1.00-5.00 |
| Magnesium stearate | 0.10-0.80 |
| Sorbityl furfural | 0.05-0.10 |
| Potassium octatrienoate | 0.05-0.50 |
| Quercetin | 0.001-0.005 |
| Catechin hydrate | 0.05-0.25 |
| Rutin | 0.15-0.60 |
| Benzoic acid | 0.2-1.50 |
| Triclosan | 0.20-0.30 |
| Boron nitride | 0.05-0.20 |
| Glycyrrhetinic acid | 0.05-0.50 |
| Titanium Dioxide Treated (Aluminum Hydroxide, Stearic acid) | 3.00-5.00 |
| Glycerin | 3.00-5.00 |
| Triethyl citrate | 0.10-0.70 |
| Aqua | q.s. 100 |

Experimental Studies

Skin Pigmentation Activity

A first experimental study is described below with reference to the attached drawings in FIGS. 1 and 2.

Materials and Methods

This experimental study on the active ingredient octatrienoic acid according to the invention was based on organ cultures of skin biopsies, which were tested in 4 groups (3 skin biopsies/well) and incubated with different concentrations of the active ingredient for 6 days.

Figure 1:
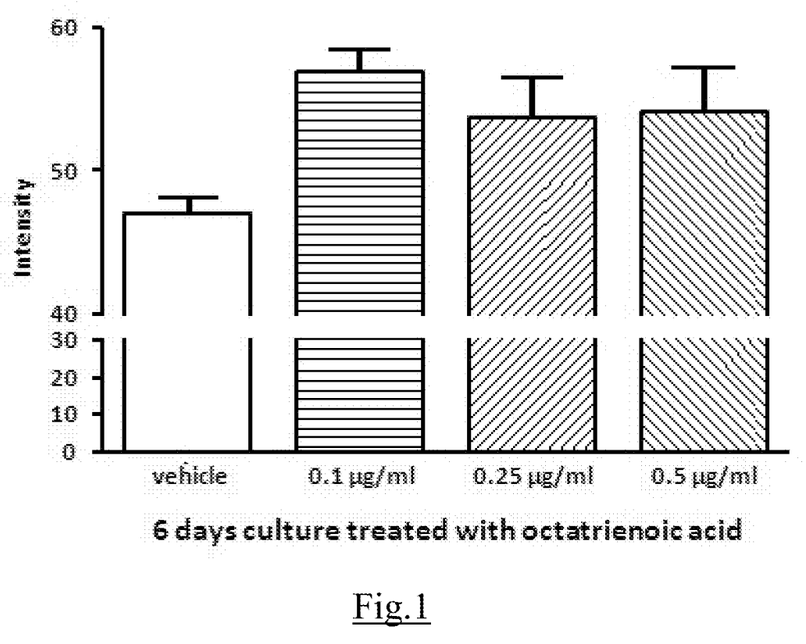
FIG. 1 is a diagram of the Masson-Fontana staining intensity in relation to the tested dose of active ingredient.

FIG. 1 is a diagram of the Masson-Fontana staining intensity in relation to the tested dose of active ingredient.

Figure 2:
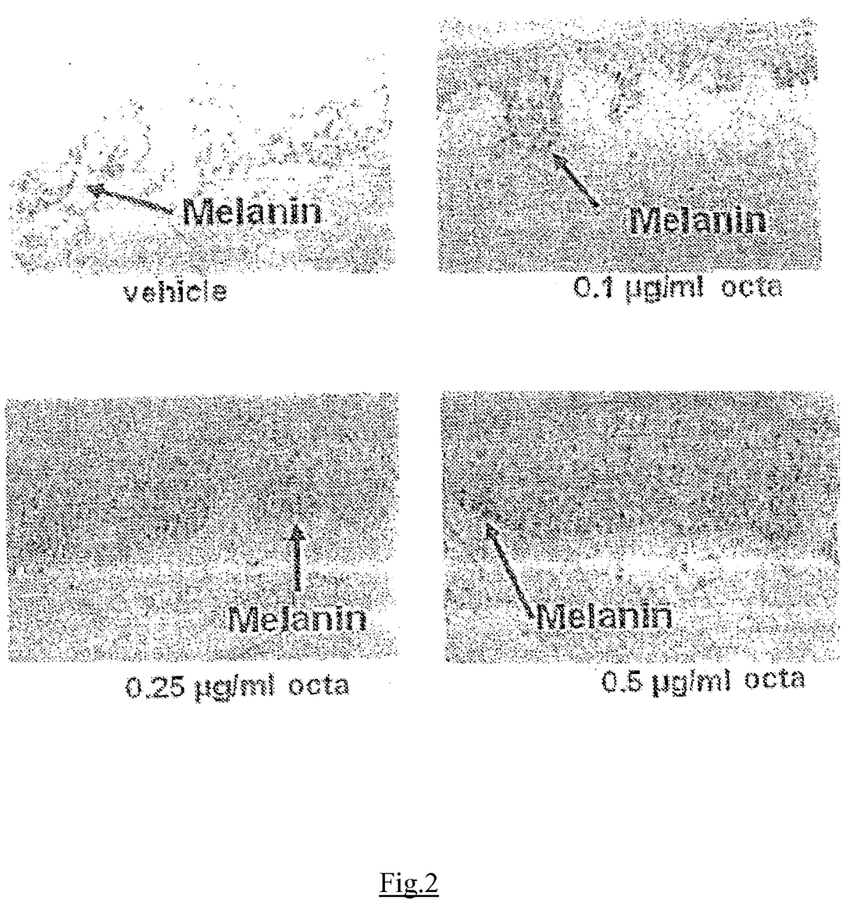
FIG. 2 shows microphotographs (enlargement×200) of pigmentation in the basal layer of the treated epidermis.

FIG. 2 shows microphotographs (enlargement×200) of pigmentation in the basal layer of the treated epidermis.

Tissue Specimens

Normal human scalp skin was obtained from a woman undergoing routine face-lift surgery, subject to her informed consent. All experiments were performed in accordance with the Declaration of Helsinki, with the approval of an ad hoc Ethical Committee.

Full-Thickness Skin Organ Culture

Biopsies 3-4 mm in size were cultured at 37° C. for 6 days in Williams' E medium (Biochrom, Cambridge, U.K.) supplemented with 100 IU mL$^{-1}$ penicillin, 10 μg mL$^{-1}$ streptomycin (Gibco, Karlsruhe, Germany), 10 μg mL$^{-1}$ insulin (Sigma, Taufkirchen, Germany), 10 ng mL$^{-1}$ hydrocortisone (Sigma) and 2 mmol L$^{-1}$ L-glutamine (Invitrogen, Paisley, UK).

Three different concentrations of octatrienoic acid (0.1 μg/mL, 0.25 μg/mL, 0.5 μg/mL) or the reference medium were administered once, at each change of medium (i.e. every 48 hours).

LDH Activity

Lactate-dehydrogenase (LDH) activity was measured every other day in the supernatant, as an indicator of cytotoxicity, according to the manufacturer's instructions (Cytotoxicity Detection Kit; Roche, Mannheim, Germany). The absorbance of the samples was measured at 490 nm using an ELISA plate reader.

Epidermal Pigmentation

For histochemical melanin assessment, Masson-Fontana staining was applied to frozen adult human scalp skin sections. Melanin stained as brown spots and the degree of pigmentation was evaluated using the quantitative Masson-Fontana test, as described elsewhere (Ito et al., 2005). This method gives a sensitive and reliable indication of changes in melanin synthesis, as shown by standard tyrosinase expression and enzyme activity assays. (Kauser et al., 2006)

Staining intensity was analysed in a previously-defined reference area of the epidermis using ImageJ software (National Institute of Health).

Statistical Analysis

The statistical analysis was performed using Student's two-tailed t-test for independent samples.

Findings

Treating the skin culture with octatrienoic acid increased the skin pigmentation at all three doses tested.

The diagram in FIG. 1 in the attached drawings shows a marked increase in the intensity of Masson-Fontana staining on day 6 of the above-described treatment, for each dose administered by comparison with the medium alone.

The photographs in FIG. 2 (enlargement×200) show the increased pigmentation in the basal layer of the epidermis on day 6 of the above-described treatment, for each dose administered, showing the areas of melanin development (see arrow).

Melanogenic Activity

A second experimental study assessed the action of the compounds according to the invention on the phenomena of melanocyte differentiation in the melanogenic process, as described below with reference to the attached drawings in FIGS. 3, 4 and 5. For this purpose, octatrienoic acid (called Octa in the diagrams, for the sake of brevity) was used on foreskin primary melanocyte cultures with varying degrees of basal pigmentation to assess the following parameters:

a) mRNA and tyrosinase protein expression, using real-time RT-PCR and Western-blot methods;
b) enzymatic activity of tyrosinase by spectrophotometry;
c) Quantification of melanin genesis by spectrophotometry.

Figure 3:
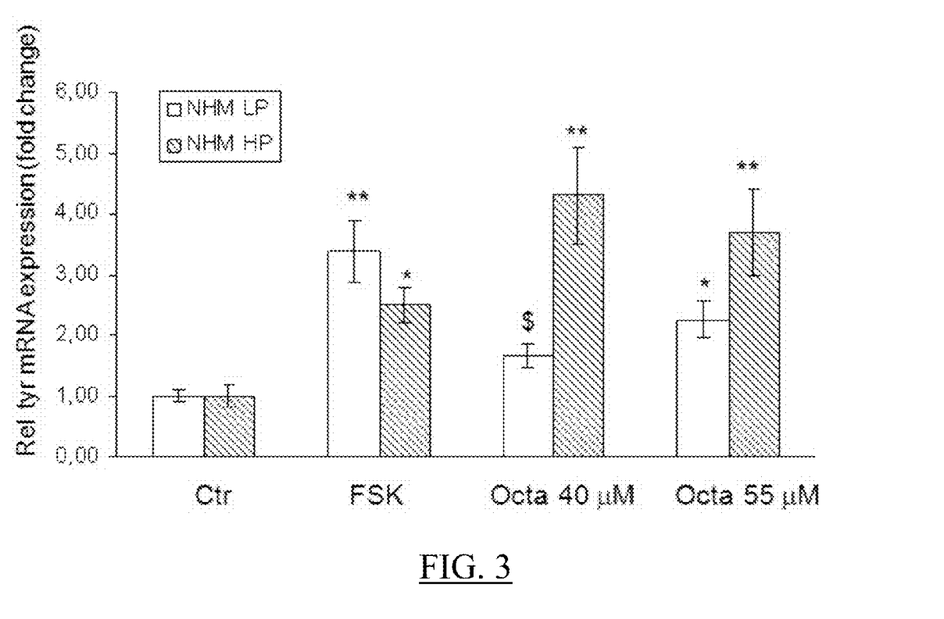

FIG. 3 shows a diagram of the results of the above-described experiment (a).

Figure 4:
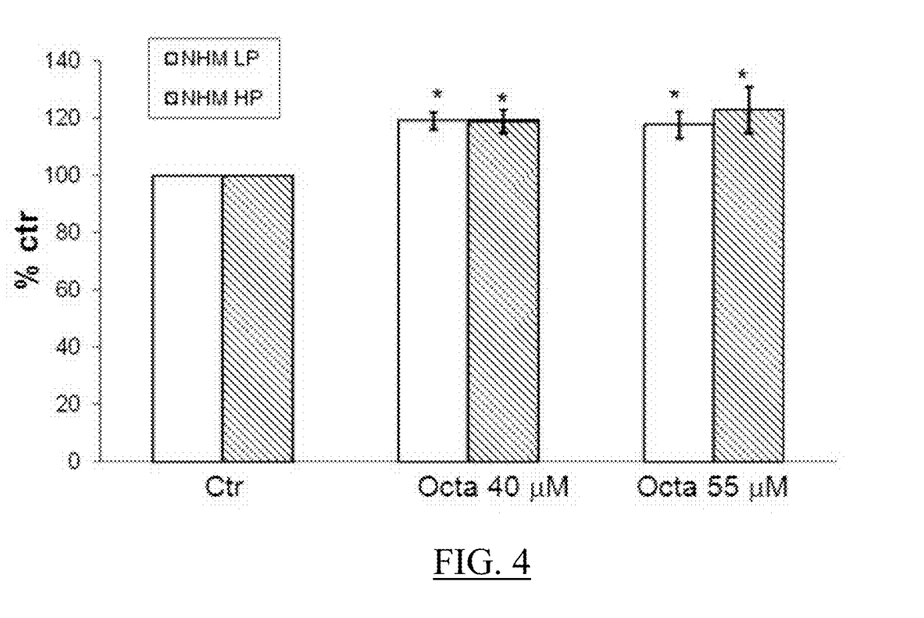

FIG. 4 shows a diagram of the results of the above-described experiment (b).

Figure 5:
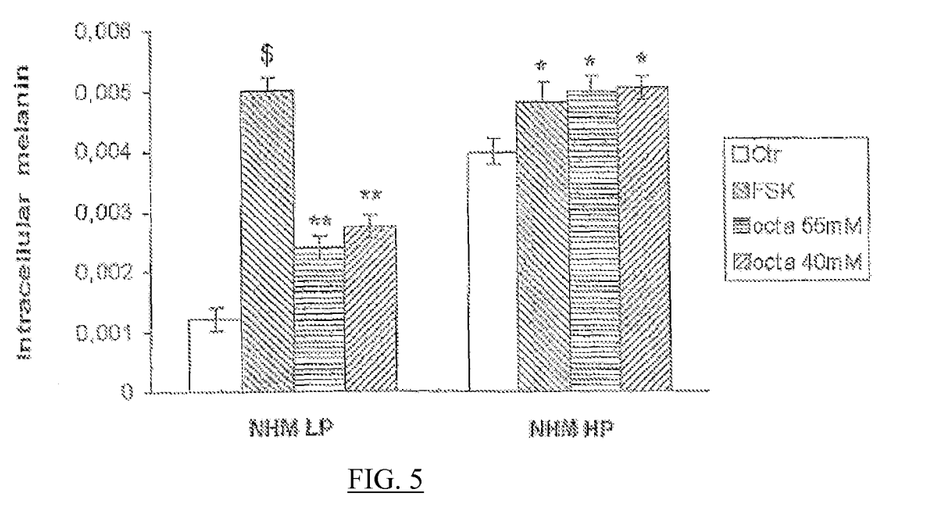

FIG. 5 shows a diagram of the results of the above-described experiment (c), as discussed below.

Analysis of Tyrosinase Expression

Tyrosinase mRNA expression was assessed by real-time RT-PCR on mRNA specimens extracted from cells after 24 h of incubation with octatrienoic acid at concentrations of 40 and 55 μm.

Forskoline (FSK), a known adenylate cyclase activator capable of promoting melanin synthesis, was used as a control for comparison with the activity of octatrienoic acid.

Each pair of columns in FIG. 3 shows the trend of tyrosinase mRNA expression (Rel tyr mRNA expression, fold change) for normal human melanocytes with a low pigmentation (NHM LP, left column in each pair) and normal human melanocytes with a high pigmentation (NHM HP, right column in each pair), for the control culture (Ctr), FSK, and the two concentrations of Octa considered. For these columns, *=p<0.01 vs. Ctr, **=p<0.001 vs. Ctr, and $=p<0.05 vs. Ctr.

As shown in FIG. 3, the experiments performed on these cultures of primary melanocytes characterised by varying degrees of basal pigmentation revealed a significant induction of tyrosinase mRNA expression following treatment with both doses of octatrienoic acid.

Western blot analysis of tyrosinase on protein extracts derived from cells treated with the same doses of Octa for 72 h confirmed that the substance tested induced melanogenic enzyme protein expression.

Analysis of Tyrosinase Activity

The activity of tyrosinase was evaluated by spectrophotometry on cell lysates derived from specimens incubated for 72 h with octatrienoic acid at concentrations of 40 and 55 μM, vs. control culture. The results given in the diagram in FIG. 4 show a significant increase in enzymatic activity, as expressed on the y coordinates as a % of the Ctr, in both the cultures of primary melanocytes with varying degrees of basal pigmentation, i.e., here again, normal human melanocytes with a low pigmentation (NHM LP, left column in each pair) and normal human melanocytes with a high pigmentation (NHM HP, right column in each pair) shown for the control culture (Ctr) and the two concentrations of Octa considered.

For these columns, *=p<0.05 vs. Ctr.

Analysis of Intracellular Melanin Content

Intracellular melanin content was assessed by spectrophotometry in cell lysates derived from specimens incubated for 72 h with octatrienoic acid at concentrations of 40 and 55 μM, as shown in FIG. 5, in normal human melanocytes with a low pigmentation (NHM LP, group of four columns on the left) and in normal human melanocytes with a high pigmentation (NHM HP, group of four columns on the right), where these columns refer to the control culture (Ctr), the reference FSK (see above) and the two concentrations of Octa considered. In FIG. 5, *=p<0.05 vs. Ctr, **=p<0.01 vs. Ctr, $=p<0.001 vs. ctr.

In the experiments performed on cultures of primary melanocytes characterised by varying grades of basal pigmentation, the results shown in the diagram in FIG. 5 revealed a significant induction of the quantity of intracellular melanins following treatment with both doses of octatrienoic acid.

Conclusions

The results obtained in the experiments performed on cultures of foreskin primary melanocytes characterised by varying degrees of basal pigmentation demonstrated the capacity of octatrienoic acid to induce the expression and activity of tyrosinase (the main melanogenic enzyme) and to increase the content of intracellular melanins.

These results prove that the compounds according to the invention are suitable for improving photoprotective capacity of the skin by means of the melanin pigmentation of the epidermis, and for increasing the intensity of skin tanning.

The invention claimed is:

1. A method for improving melanin pigmentation of the skin of a human subject in need thereof, by administering to the human subject a composition comprising one or more of the compounds having general formula (I) as the active ingredient $$CH_3-(CH=CH)_n-R \quad (I)$$

where: n=3, 5, 7; R is chosen from $-CH_2-O-CO-R'$, $-CO-OR'$ or $-CO-O^{(-)}$, R' is chosen from H, $C_1$-$C_{22}$alkyl or alkenyl, aryl or aralkyl, or sugars, and their pharmaceutically acceptable salts.

2. A method for providing photoprotective capacity to human skin by improving melanin pigmentation of the epidermis, by administering to a human subject in need thereof a composition comprising one or more of the compounds having general formula (I) as the active ingredient $$CH_3-(CH=CH)_n-R \quad (I)$$

where: n=3, 5, 7; R is chosen from $-CH_2-O-CO-R'$, $-CO-OR'$ or $-CO-O^{(-)}$, R' is chosen from H, $C_1$-$C_{22}$alkyl or alkenyl, aryl or aralkyl, or sugars, and their pharmaceutically acceptable salts.

3. The method according to claim 1, wherein the compound is 2,4,6-octatrienoic acid.

4. The method according to claim 1, characterized in that the composition is formulated in a composition for topical administration.

5. The method according to claim 1, characterized in that the composition is formulated for topical administration, and includes the compound in a quantity in the range of 0.01 to 2.0% w/w.

6. The method according to claim 2, wherein the compound is 2,4,6-octatrienoic acid.

7. The method according to claim 2, wherein the composition is formulated in a composition for topical administration.

8. The method according to claim 2, wherein the composition is formulated for topical administration, and wherein the composition includes the compound in a quantity in the range of 0.01 to 2.0% w/w.

9. The method according to claim 1, wherein the human subject is treated for a disorder from among the group consisting of vitiligo, pityriasis alba, idiopathic guttate hypomelanosis, post-inflammatory hypopigmentation, Bourneville's syndrome (tuberous sclerosis) and Tinea versicolor.

10. The method according to claim 1, wherein the improvement in melanin pigmentation of the human skin produces an improvement in tanning of the human skin.

* * * * *